United States Patent [19]

Gordon

[11] Patent Number: 4,496,538

[45] Date of Patent: Jan. 29, 1985

[54] HAEMOPHILUS INFLUENZAE B POLYSACCHARIDE-DIPHTHERIA TOXOID CONJUGATE VACCINE

[75] Inventor: Lance K. Gordon, Mount Pocono, Pa.

[73] Assignee: Connaught Laboratories, Inc., Swiftwater, Pa.

[21] Appl. No.: 395,743

[22] Filed: Jan. 6, 1982

[51] Int. Cl.³ .................. A61K 39/102; C07G 7/00
[52] U.S. Cl. ........................ 424/92; 260/112 R; 536/1.1; 424/88
[58] Field of Search ............. 424/85, 87, 88, 92; 2/180; 260/112 R; 536/123, 127, 1.1

[56] References Cited

U.S. PATENT DOCUMENTS 4,196,192  4/1980  Kuo ............................. 424/92
4,210,641  7/1980  Brossard et al. ............... 424/180
4,220,717  9/1980  Kuo ............................. 424/92

OTHER PUBLICATIONS

Schneerson et al., *J. Exp. Med.*, vol. 152, No. 2, pp. 361-376, 1980.
Anderson et al., *J. Infect. Dis.*, vol. 146, No. 6, pp. 530-538, 1981.

*Primary Examiner*—Blondel Hazel
*Attorney, Agent, or Firm*—Wegner & Bretschneider

[57] ABSTRACT

A water-soluble covalent polysaccharide-diphtheria toxoid conjugate having a molecular weight between 140,000 and 4,500,000 dalton and a ribose/protein ratio between 0.25 and 0.75, capable of producing T-cell dependent antibody response to polysaccharide from *H. influenzae* b, prepared by mixing a derivatized diphtheria toxoid in a substantially cyanogen halide-free solution with a cyanogen halide-activated capsular *H. influenzae* b polysaccharide hapten consisting of approximately equal parts of ribose, ribitol and phosphate, which polysaccharide had previously been heat sized until more than 60% attained a molecular size between 200,000 and 2,000,000 dalton.

3 Claims, 2 Drawing Figures

HAEMOPHILUS INFLUENZAE B POLYSACCHARIDE-DIPHTHERIA TOXOID CONJUGATE VACCINE

BACKGROUND OF THE INVENTION

*Haemophilus influenzae* b is the most common cause of bacterial meningitis and other invasive infections in children in the United States. Extrapolating from prospective data gathered in Fresno County, Calif., approximately one in 300 newborns in the United States will develop bacteritic *H. influenzae* disease before the age of five years, and two-thirds of these episodes are associated with meningitis. Despite therapy with antibiotics, the mortality of Haemophilus meningitis remains at approximately 5%, and serious neurologic sequalae occur in as many as 10 to 25% of survivors. Since 1974, strains of Haemophilus resistant to ampicillin have emerged in the United States. By 1981 these strains were prevalent in nearly all communities, and b Haemophilus strains resistant to chloramphenicol or to multiple antibiotics have also been described. Recently, type b Haemophilus has been implicated as a cause of epidemic disease in children attending day care centers, a problem which appears to be increasing in direct proportion to the increase in the number of women entering the work force. These concerns have heightened interest in developing a vaccine for prevention of systemic Haemophilus infections in infants and young children.

Considerable data indicate that the type b capsule of *Haemophilus influenzae,* a heteropolymer of approximately equal amounts of ribitol, ribose and phosphate (PRP), is an important determinant of virulence, enabling the organism to resist host defenses. Antibodies directed at the type b capsule confer protection against disease by initiating opsonization and complement-dependent bacteriolysis. During the last three decades, considerable effort has been made to purify and characterize this capsular polysaccharide. A type b capsular polysaccharide vaccine was prepared which was immunogenic in adults and in children older than 18 months of age, but failed to elicit immunity in infants, the age group at greatest risk of Haemophilus disease. (Makela, P. M. et al., J. Infect. Dis. 136: S43; 1977).

The purified type b polysaccharide appears to act as a thymic-independent antigen. Booster immunization does not result in either a memory or an accelerated antibody response (Anderson, P. et al., J. Infect. Dis. 136, S57; 1977).

The carrier-hapten concept was established by Landsteiner in 1926, and a general method used to create a covalent link between PRP and a protein carrier was published by Schneerson et al. in 1980 (J. Exp. Med. 152, 361; 1980). In such a vaccine an antigenic, but weakly or non-immunogenic molecule, a hapten, contributes a new antigenic specificity to an immunogenic carrier molecule.

SUMMARY OF THE INVENTION

The invention relates to a new *Haemophilus influenzae* b polysaccharide-diphtheria toxoid conjugate (PRP-D) vaccine, the polysaccharide hapten used for making same and the process for producing them. More specifically the invention provides a pure *Haemophilus influenzae* b polysaccharide of a molecular size principally between 200,000 and 2,000,000 dalton which is activated with cyanogen halide, typically the bromide. The activated polysaccharide is intimately mixed with a toxoid, preferably diphtheria toxoid, to effect conjugation. Preferably, the toxoid is derivatized using as a spacer a bridge of up to 6 carbons, such as provided by use of the adipic acid hydrazide derivative of diphtheria toxoid (D-AH).

By use of this method there is obtained a conjugate vaccine which elicits a T-cell dependent response to polysaccharide from *Haemophilus influenzae* b.

DISCLOSURE OF THE INVENTION

Figure 1:
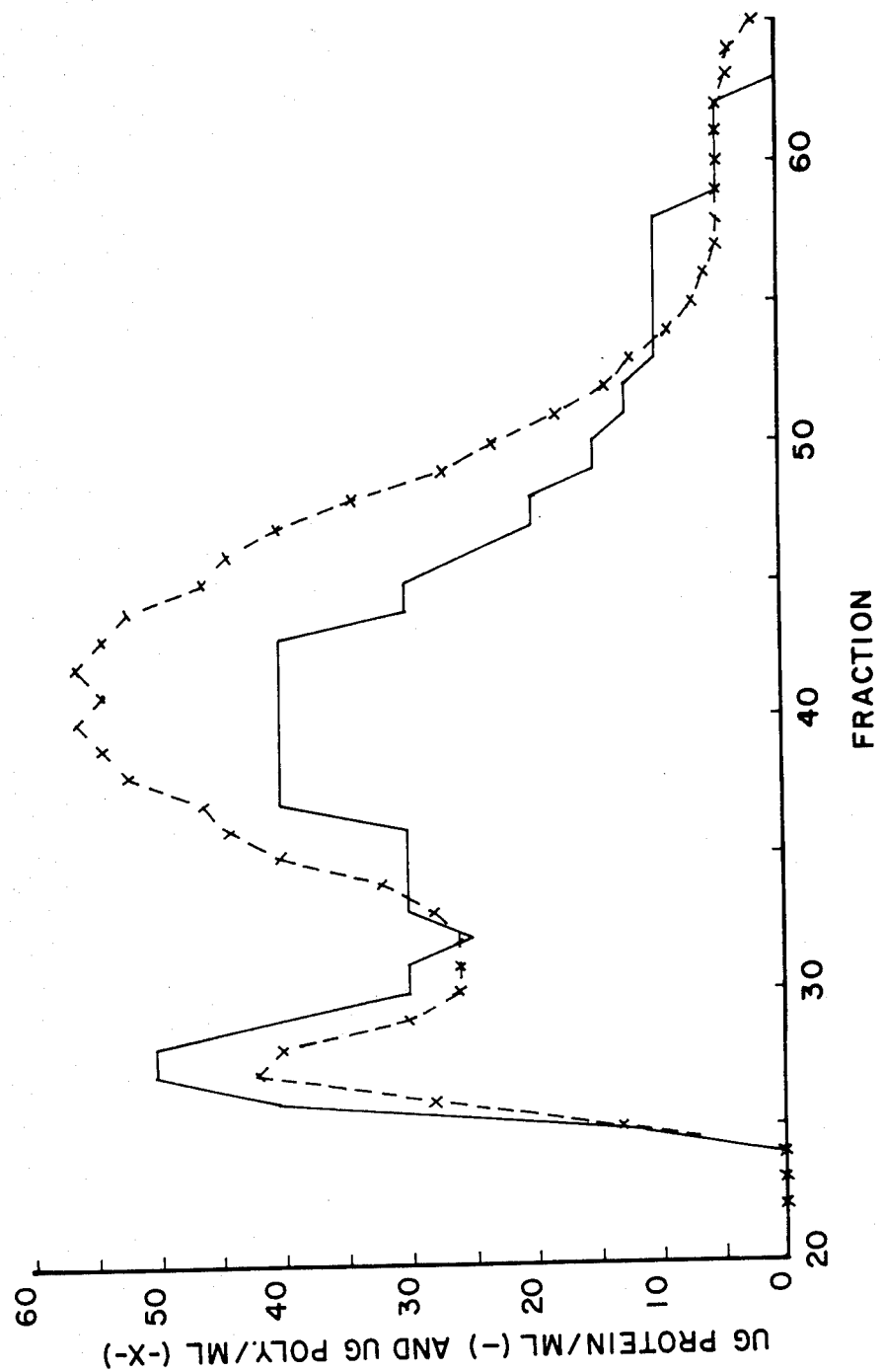
FIG. 1 graphically illustrates the chromatographic profile for the bulk polysaccharide-diphtheria toxoid conjugate (PRP-D) of Example IV.

The development of stable humoral immunity requires the recognition of foreign material by at least two separate sets of lymphocytes. These sets are the B-lymphocytes, which are the precursors of antibody forming cells, and the T-lymphocytes which modulate the function of B-cells. While some antigens, including several polysaccharides, are capable of directly stimulating B-cells to produce antibody (T-independent antigens), most antigens (T-dependent) must be presented to the B-cell by a T-lymphocyte. In the case of the vaccine of this invention, the diphtheria toxoid portion of the vaccine is recognized by the T-cell system. Since the protein carries both its own antigenic determinants and the covalently bound PRP hapten, both sets of determinants should be presented by T-cells to B-cells. The result of administration of this carrier-hapten preparation is that PRP is presented as a T-dependent immunogen. There is good reason to expect that a T-dependent presentation of PRP will induce protective immunity in infants, the target population at greatest risk.

T-independent antigens induce B-cells to terminally differentiate into antibody secreting cells (plasma cells), while T-dependent responses are considerably more complex. After receiving a T-dependent stimulus, the B-cell population enters not only antibody production, but also proliferation and maturation. As a result, there should be an increase in the number of B-cells making antibodies to PRP and an increase in the number of B-cells capable of responding to a second exposure to PRP. Repeated immunization should result in further increases in the number of PRP specific B-cells and, consequently, higher antibody titers, a booster response. In summary, while T-independent responses are limited by the number of responsive B-cells, T-dependent responses result in an increase in the total number of antigen responsive cells.

The vaccine of this invention, PRP-D, has been shown to function as a T-dependent immunogen in laboratory animals. Thirteen out of thirteen rabbits serially immunized with a standard dose of PRP-D showed booster responses. In addition, primary immunizations with the carrier protein, diphtheria toxoid, were shown to augment the initial response to the PRP component of the PRP-D conjugate. A similar augmentation of the PRP response was not seen in animals primed with tetanus toxoid.

The vaccine of this invention is a PRP-D hapten-carrier conjugate. In such vaccines, the antigenic but weakly immunogenic hapten molecule (PRP) contributes a new antigenic specificity to a highly immunogenic carrier molecule (D).

The purified diphtheria toxoid (D) used as carrier in the preparation is a commercial toxoid modified (derivatized) by the attachment of a spacer molecule, such as adipic acid dihydrazide (ADH), using the water-soluble carbodiimide condensation method. The modified toxoid, typically the adipic hydrazide derivative D-AH, is then freed from unreacted ADH.

*Haemophilus influenzae* b capsular polysaccharide is prepared from commercial sources such as used for licensed polysaccharide vaccines. However, while the polysaccharide is conventionally purified as a calcium salt, the use of calcium ions is avoided because they interfere with the use of carbonate buffer in the conjugation procedure. The molecular size of the polysaccharide is then adjusted by heating until the desired dimension for the hapten is obtained. Typically, heating of the liquid polysaccharide for 15 minutes at 100° C. suffices to assure that less than 20% of the molecules are of a molecular size smaller than 200,000 dalton and less than 20% of a molecular size greater than 2,000,000 dalton. This sizing operation is important to obtain a proper PRP-D from unreacted protein.

The sized polysaccharide thus obtained is activated with cyanogen halide, typically bromide, to create an electrophilic group on the polysaccharide. Unreacted cyanogen halide is exhaustively removed because, if there is a substantial residue, it causes cross-linking of the protein in the following reaction mixture. The resulting cross-linked product traps polysaccharide, producing a higher molecular weight conjugate which is different in chemical properties from the conjugate produced herein and a vaccine which lacks the desirable proportion of the vaccine of this invention.

The activated PRP and D-AH are then combined and allowed to react in the cold. Some of the hydrazide groups on the derivatized diphtheria toxoid react with the activated sites on PRP to form covalent bonds. The product is PRP covalently bound to derivatized D through a six carbon chain. This reaction product is purified by gel permeation chromatography to remove any unreacted protein and low molecular weight contaminants of molecular weight lower than 140,000 dalton. The typical molecular weight of the principal fraction is about 675,000 dalton relative to dextran standard. A typical range for relative molecular size is 140,000 dalton to 4,500,000 dalton.

A preservative such as thiomerosal is added, in the case of thiomerosal, to a final concentration of 1:10,000. The bulk concentrate (PRP-D) is filtered through a 0.2 micron Durapore membrane and stored in the cold.

The following examples are provided for purposes of illustrating the invention in further detail. They are not to be construed as limiting the invention in spirit or in scope.

EXAMPLE I

Preparation of PRP Used

A. Organism

Capsular polyribosyl ribitol phosphate (PRP) of *Haemophilus influenzae* b was prepared from the commercially used Eagan strain. The culture was repeatedly transferred and a lyophilized seed prepared. From this lyophilized seed one additional transfer was made to prepare wet working seeds (stored at −60° C.). Fermenter lots of bacterial cells were prepared from the wet working seed.

Culture purity is determined by the following criteria:

1. negative Gram stain characteristics;
2. growth on agar containing NAD (diphosphopyridine nucleotide) and Hemin (Bovine Type I crytalline salt of ferriheme);
3. failure to grow on agar without NAD or Hemin; and
4. agglutination by specific antisera (type b *Haemophilus influenzae* b, Hyland Laboratories).

B. Cultivation and Media

For subculturing the bacterium, i.e., preceding inoculation of a fermenter, BHI Agar (per liter: 37 gm BHI Difco, 15 gm Bacto Agar Difco, 0.6 ml 1% NAD Sigma-Grade III and 6 ml of 0.2% Hemin (Sigma-Bovine Type 1) was employed. Cells (20 hours) washed from an agar surface are used to inoculate *Haemophilus influenzae* b (Hib) liquid media (1 liter aliquots); these cultures are incubated with shaking until the bacterium reaches the log phase of its growth cycle. At this time, 2 liters of culture are used to inoculate each 40 liters of liquid Hib media in a fermenter and 300 ml 8% UCON (Union Carbide lubricant) is added. After 16 to 18 hours, the fermenter culture is ready for harvest.

The composition of the Hib liquid media per 1000 ml is:

| | |
|---|---:|
| Yeast Extract Dialysate, Difco | 5.0 gm |
| Casamino Acids, Difco | 22.5 gm |
| Sodium Phosphate, dibasic | 14.4 gm |
| Dextrose | 5.59 gm |
| Hemin | 20 gm |
| Ammonium Hydroxide (30%) | 0.1534 ml |
| NAD 1% | 0.6 ml |

When harvesting a fermenter, culture purity is determined by appropriate Gram staining and culturing techniques (see above). Cetavlon (hexadecyltrimethylammonium bromide) is added to the culture to a final concentration of 0.1%. After 30 minutes, at which time the bacteria have been inactivated, the solid paste is collected by centrifugation. The wet paste is stored at −70° C. until further processing.

C. Purified Polysaccharide

The extraction and subsequent purification of the PRP is carried out using the following procedure:

1. Dissociation from Detergent

For each gram wet weight of paste, 10 ml of 0.4M NaCl is added. The suspension is mixed in a commercial blender for 30 seconds. The mixture is centrifuged for 15 minutes at 17,000 Xg in the cold (4° C.). The supernatant is collected and ethanol is added to a concentration of 25%. This material is then centrifuged for 2 hours at 17,000 Xg (4° C.) and the supernatant saved. Ethanol, at four times the volume of the supernatant, is added and the material held overnight at 4° C.

2. Removal of Nucleic Acids

The material is centrifuged for 5 minutes at 2800 Xg (4° C.). The sediment is collected and resuspended in Tris-MgSO$_4$ buffer at one-fourth the volume originally used to extract the paste. The composition of the Tris buffer is as follows per liter of distilled water:

| | |
|---|---|
| tris-hydroxymethylamino-methane (Sigma) | 6 gm |
| MgSO$_4$.7H$_2$O | 246 mg |
| thimerosal (Elanco) | 50 mg |

The pH is adjusted to 7.0±0.2 with concentrated hydrochloric acid.

Deoxyribonuclease I 1.5 mg (Sigma D-0876) and ribonuclease-A 0.75 mg (Sigma-Type 1-AS, R-5503) per 100 gm of original wet paste are added. The material is placed in a dialysis bag and incubated for 18 hours at 37° C. versus 18 liters of Tris-MgSO$_4$ buffer.

3. Removal of Proteins

The material is further processed to remove protein components by adding an equal volume of phenol-acetate solution (135 ml of 10 percent (w/v) sodium acetate combined with 454 gms of phenol, AR grade). The materials is then shaken for 30 minutes (4° C.), centrifuged for 15 minutes at 17,000 Xg and the aqueous phase collected. Two additional phenol extractions are conducted followed by dialysis of the last aqueous phase versus distilled water.

The material at this stage constitutes the bulk liquid capsular polysaccharide (PRP) and is stored at −20° C. until further processing (Section D below).

4. Assessment of Quality of Polysaccharide

The quality of the bulk PRP is judged based on the analysis of a liquid sample that is removed. Ethanol is added (4 volumes), then CaCl$_2$ (final concentration of 0.02M) and the PRP is precipitated. The PRP is sedimented by centrifugation and dried under vacuum over a dessicant. A thermogravimetric analysis (TGA) is used to determine the moisture content. Further analyses are calculated on a dry weight basis.

Criteria for acceptance include:
(a) analysis of ribose (Orcinol method): greater than 30 percent,
(b) analysis of protein (Lowry method): less than 1 percent,
(c) analysis of nucleic acids (U.V. adsorbance): less than 1 percent, and
(d) precipitation with specific immune sera by the (counterimmunoelectrophoresis method).

In addition, the molecular size is determined by suitable gel premeation chromatography. The polysaccharide is monitored for endotoxin by Limulus Lysate testing and by rabbit pyrogenicity testing.

A typical lot has the following characteristics:
(a) Protein content, 0.5%
(b) Nucleic acid content, 0.35%
(c) Residual bovine antigens: No contamination of the purified PRP by bovine RNA-ase and DNA-ase used in preparation of the polysaccharide, as measured by radioimmunoassay.
(d) Endotoxin content was measured by the Limulus Amoebocyte to Lysate Assay (LAL): 200 ng/mg PRP.
(e) Kd on CL-4B Sepharose: 0.30. A value of 0.30 corresponds to an approximate molecular weight of 1,125,000 relative to dextran standards.

D. Preparation of Polysaccharide (PRP) Reagent

The polysaccharide is thus purified as a liquid, but calcium is not used in the purification procedure. (Conventional polysaccharide purification yields a calcium salt, but calcium can combine with the carbonate buffer used hereinbelow during conjugation to form a precipitate.)

The size of the polysaccharide is adjusted by heating at 100° C. for a time proportional to the degree of size change needed. Size of the polysaccharide is adjusted so that less than 20% elutes from a CL-4B Sepharose column in the void volume, and less than 20% elutes with a Kd greater than 0.5. The principal fraction has a molecular weight of 205,000 to 2,000,000 dalton.

EXAMPLE II

Activation of PRP

A. This polysaccharide is cooled on an ice bath to 4° C. in a reaction vessel equipped with a magnetic stirrer. The initial volume of PRP at the concentration of 25 mg/ml (20–30 mg/ml range) in distilled water is recorded. Then sodium chloride is added to a concentration of 0.85%.

B. The pH of the polysaccharide is raised to 10.5–11.0 by addition of 1N sodium hydroxide. (This range is chosen because at a lower pH there is less reaction with cyanogen bromide and at higher pH the polysaccharide breaks down.)

C. Dry cyanogen bromide is dissolved in 0.005N sodium bicarbonate buffer of pH 10.5–11.0 and immediately (within 10 minutes of preparation) is added to the reaction vessel in a proportion of 0.4 mg/mg PRP.

D. The pH of the mixture is adjusted to and maintained at 10.5–11.0 for 6 minutes by addition of sodium hydroxide.

E. The pH is then dropped to 6.0 with 1N HCl. (Acid pH stabilizes the activated sites created on the polysaccharide by cyanogen bromide. Lowering the pH further results in hydrolysis of the PRP.)

G. There is added an equal volume of saline, pH 6.0, prechilled to 4° C.

H. The cyanogen bromide-polysaccharide mixture is transferred to a concentrator apparatus and concentrated to the initial volume recorded at step A.

I. Steps G and H are repeated at total of 10 times. Thus about 99.9% of the unconsumed cyanogen bromide is removed while the polysaccharide concentration is maintained at 25 mg/ml. If the cyanogen bromide is not removed, it reacts with the diphtheria toxoid used below.

EXAMPLE III

Preparation of D-AH Carrier

A. Commercial diphtheria toxoid (D) in distilled water is concentrated to 25 mg/ml over a membrane that retains molecules over 10,000 dalton in a positive pressure stirred concentrator.

B. A dry mixture of 8 mg adipic acid dihydrazide (ADH) per mg protein and 0.75 mg 1-ethyl-3-(3-dimethylaminopropyl)carbodiimide (EDAC) per mg protein are placed in a reaction vessel equipped with an efficient stirrer and a pH probe to permit monitoring and control of pH.

C. The diphtheria toxoid is then added to the reaction vessel making the proportion of the reactants:

| | |
|---|---|
| diphtheria toxoid = | 25 mg protein/ml |
| ADH = | 8.0 mg/mg protein |
| EDAC = | 0.75 mg/mg protein |

(The use of acetate buffer on sequential addition of ADH and EDAC results in a persistent flocculent precipitate. The reactants have a sufficient buffering capacity of their own.)

D. The pH is immediately adjusted to 4.7 and maintained at 4.7±0.2 for a minimum of 2 hours.
  1. The course of the chemical reaction can be followed on the recorder of the pH controller. If necessary, the reaction is allowed to proceed past 2 hours until the pH is stable for at least 15 minutes, (i.e., 15 minutes without needing HCl addition to control pH).
  2. The amount of HCl consumed is recorded as a process check.
  3. Temperature change in the reaction vessel is also monitored.

E. The reaction product is dialyzed at 4° C. against two changes of saline, a minimum 100 volumes and 8 hours per change.

F. It is then dialyzed against two changes of phosphate buffered saline, minimum volume, time and temperature as for step E.

G. The product (D-AH) is concentrated back to 25 mg/ml protein with a positive pressure apparatus and 10,000 MW membrane.

H. The concentrate is sterile filtered (0.2μ) and stored at 4° C.

Assay of a sample of a typical lot of such D-AH carrier showed a ratio of 38.3 microgram ADH/mg DT. Chromatography of that sample showed a Kd value on CL-4B Sepharose of 0.75 which corresponds to an approximate molecular weight of 139,000 relative to protein standards.

EXAMPLE IV

Formation of the Covalent

Polysaccharide-diphtheria Toxoid Conjugate (PRP-D)

A. The diphtheria toxoid adipic acid hydrazide carrier (D-AH) of Example III, at a concentration of 25 mg/ml, is treated with sodium bicarbonate to a concentration of 0.5M and the pH is adjusted to 8.5. (Significantly lower salt concentrations result in the formation of a gel in the final reaction mixture with activated polysaccharide.)

B. In a reaction vessel which can be sealed, an equal amount of the washed PRP solution produced in Example II is added and the pH should be stable at 8.4–8.6. (If CNBr has not been removed, the pH will drift rapidly downward and a copious precipitate will form. This reaction occurs even in the absence of polysaccharide. There should not be a significant change of the physical appearance of the reactants on combination.)

C. The reaction mixture is tumbled for 15–18 hours at 4° C.

D. The conjugate is purified by gel permeation chromatography on Sephacryl-300 equilibrated in phosphate buffered saline to remove unreacted protein and low molecular weight material (less than 140,000 dalton). (If the starting polysaccharide is too small it will not be possible to separate the conjugate from free protein in this manner.)

E. Samples of this purified conjugate are removed for chemical analysis, described in the following section of this example.

F. Thimerosal is added to the purified conjugate to a concentration of 1:10,000 and the product is stored at 4° C. until analysis.

G. The product is 0.2 micron sterile filtered. (If the polysaccharide is not sized as described in Example I(D), i.e., if it is oversize, the resulting conjugate will not be filterable.)

Analysis

Tests performed on the bulk concentrate of Example IV gave the following results:
  (a) Ribose content: 156.5 microgram/ml.
  (For the calculation of PRP values in Example V, a conversion factor of 2 is used to calculate a nominal polysaccharide concentration based on the empirically determined ribose concentration.)
  (b) Protein content: 330 microgram/ml.
  (c) Ribose/protein ratio: 0.47 (limits 0.25–0.75)
  (d) Chromatographic analysis on Sepharose CL-4B gave the chromatographic profile of FIG. 1. The solid line shows the curve for microgram protein/ml, the broken line that for polysaccharide/ml.
  (e) Kd (polysaccharide): 0.36
  Determined by individual fraction ribose assay for PRP. A value of 0.36 corresponds to an approximate molecular weight of 674,000 relative to dextran standards.
  (f) Kd (protein): 0.34
  Determined by individual fraction Lowry assay for protein. The change in the Kd value of the diphtheria toxoid from 0.75 to 0.34 shows that the conjugation of protein with polysaccharide forms a molecule which is chromatographically different from either raw material.
  (g) Free Protein: Less than 5%.
  Free protein represents derivatized diphtheria carrier protein which as not been bound to PRP. It is determined by comparing the amount of protein that elutes in the position of a diphtheria toxoid sample relative to the total eluted protein.
  (h) Endotoxin Content: 1 ug/ml
  Endotoxin was quantitated by the Limulus Amoebocyte to Lysate Assay (LAL). The endotoxin content amounts to 64 ng per 10 ug ribose human dose of PRP-D.
  (i) Pyrogenicity:
  The bulk concentrate meets the standards for pyrogenicity set forth in 21 CFR 610.13(b) using a weight equivalent (human) dose of 0.15 ug ribose per milliliter per kilogram body weight of rabbit.
  (j) Polyacrylamide Gel Electrophoresis (PAGE):
  PAGE analysis was performed to obtain supporting evidence of purity and covalent bonding between polysaccharide and protein. While free carrier bands just over halfway into the rod gel, at approximately the position of catalase (60,000 MW), the PRP-D conjugate was not able to enter the gel (prior to the position of thyroglobulin, 330,000 MW). PRP-D showed a single band at the origin.
  (k) Cyanogen Bromide:
  While cyanogen bromide (CNBr) is used in the first steps before preparing a PRP-D conjugate, it is subsequently excluded from the product. Several steps of the process contribute to the reduction of CNBr content. However, final purification of the vaccine by gel permeation chromatography removes any contaminants below 100,000 MW. This purification precludes contamination with residual traces of free CNBr or its degradation products.

EXAMPLE V

PRP-D Immunogenicity Testing

This experiment was designed to show T-cell dependency as evidenced by: carrier dependency, carrier specificity, booster effect, and Ig class switch. This experiment was carried out in two parts: (1) an initial priming sequence of two injections; (2) a challenge sequence of two injections.

Materials

1. PRP-D Bulk concentrate, Example 4.
2. Tetanus Toxoid (TT).
3. Diphtheria Toxoid (DT).
4. *H. influenzae* b capsular polysaccharide (PRP).
5. PRP/DT, a mixture of 20 ug PRP (10 ug ribose) and 20 ug DT.
6. PRP/DT-AH, a mixture of 20 ug PRP (10 ug ribose) and 20 ug DT-AH.

Method

All immunizations were administered subcutaneously without adjuvant in 1 ml volumes. All doses containing PRP were adjusted to 10 ug ribose per 1 ml dose. Unconjugated toxoic doses were adjusted to 20 ug protein per 1 ml dose. A rotating schedule was used with immunizations spaced 14 days apart. Each immunization was followed by a bleed 10 days later. All preparations were diluted in phosphate buffered saline containing 0.01% thimerosal. Aliquots were prepared as four dose vials, and stored at −20° C. Three rabbits were immunized in each group.

Serology

Sera were assayed by the solid phase radioimmunoassay (SPIRIA) for anti-PRP, anti-DT-AH, anti-DT, and anti-TT as indicated. Antibodies levels were quantitated as microgram IgG and IgM per ml.

|  |  |  | Protocol: |  |  |  |
|---|---|---|---|---|---|---|
| Group | Primary | Secondary | PRP | SPRIA DT-AH | DT | TT |
| 1 | PRP | PRP | + |  |  |  |
| 2 | TT | PRP-D | + | + | + | + |
| 3 | DT | PRP-D | + | + | + | + |
| 4 | PRP/DT | PRP-DT | + |  | + |  |
| 5 | PRP/DT-AH | PRP/DT-AH | + | + |  |  |
| 6 | PRP-D | PRP-D | + | + | + |  |

Schedule

Rabbits were pre-bled and immunized according to group every 14 days. Each immunization was followed by a post-bleed 10 days later. The first two injections were made with the primary immunogen, while the third and fourth injections were made with the secondary immunogen.

Figure 2:
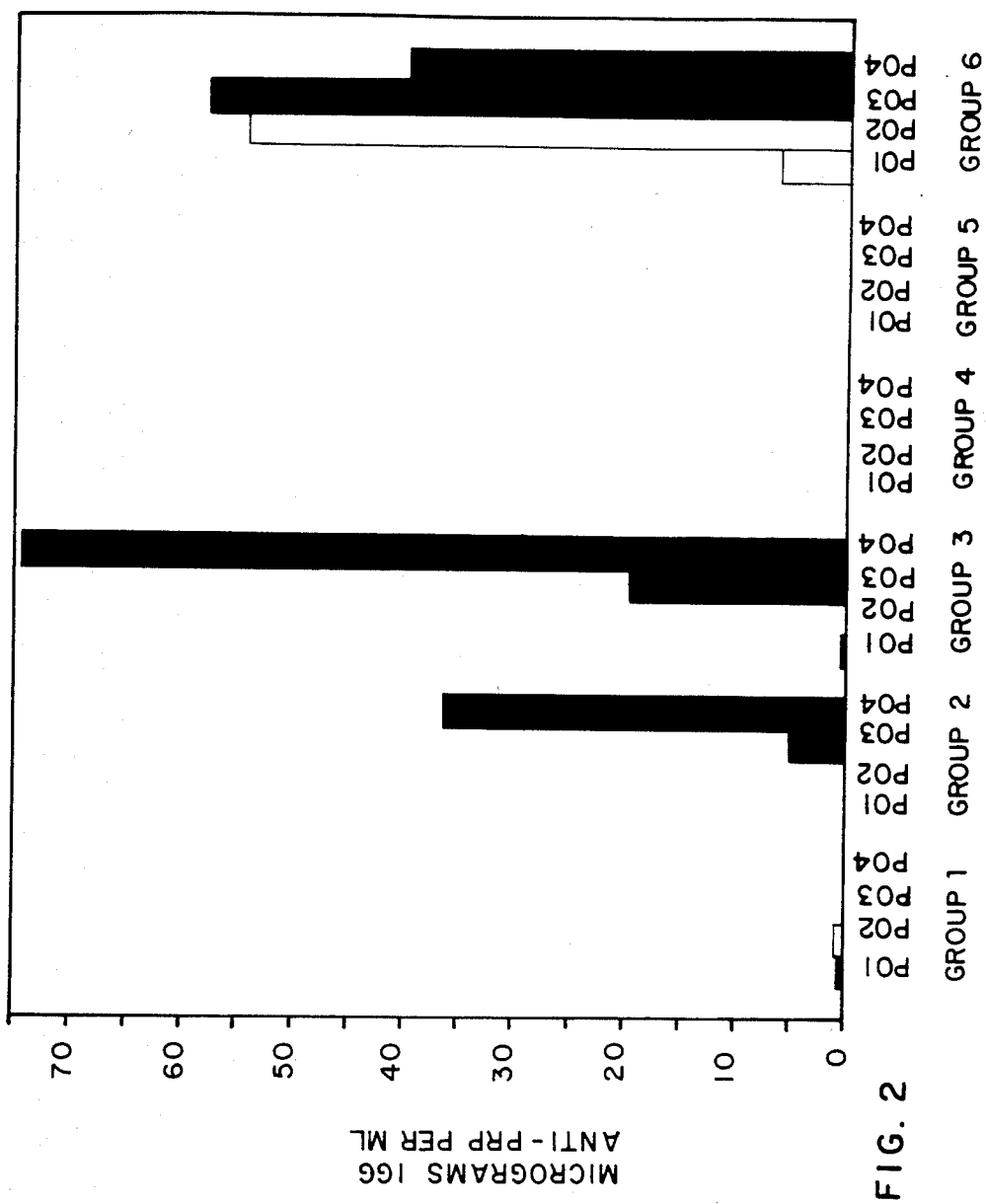
FIG. 2 demonstrates the immunogenicity of *Haemophilus influenzae* b capsular polysaccharide, i.e., the anti-PRP response. This bar graph presents the data of Table 1, according to the protocol of Example V.

Anti-PRP response is demonstrated in FIG. 2, below. The mean level of IgG antibody to *Haemophilus influenzae* b capsular polysaccharide in the six experimental groups of rabbits (three animals per group) are graphically illustrated. Groups are labelled on this figure in accordance with the above protocol. Prebleed levels were less than 1 μg/ml for all rabbits and are not shown in this figure for clarity.

Open bars represent the level of IgG following two successive injections with the primary immunogen. Solid bars show the IgG levels following the third and fourth injections which were with the secondary or challenge immunogens.

IgG responses were seen only following immunization with the PRP-D conjugate vaccine. Priming the rabbits in group 3 with diphtheria toxoid accelerated the response to PRP-D, while priming the tetanus toxoid (group 2) had no effect.

These results are included in Table 1.

TABLE 1

ANTI-PRP RESPONSE
Solid Phase Radioimmunoassay for IgM and IgH

|  |  | PRP | | Diphtheria Toxoid | | Tetanus Toxoid | |
|---|---|---|---|---|---|---|---|
|  |  | IgG* | IgM | IgG | IgM | IgG | IgM |
| Group 1 | Pre | 0.0# | 0 | ND% |  | ND |  |
|  | Post 1 | 0.33 ± 0.58 | 0 |  |  |  |  |
|  | Post 2 | 0.8 ± 1.39 | 0 |  |  |  |  |
|  | Post 3 | 0 | 0 |  |  |  |  |
|  | Post 4 | 0 | 0 |  |  |  |  |
| Group 2 | Pre | 0 | 0 | 0 | 0 | 0.5 ± 0.87 | 0 |
|  | Post 1 | 0 | 0 | 0 | 0 | 25.1 ± 15.10 | 113.1 ± 129.54 |
|  | Post 2 | 0 | 0 | 0 | 0 | 112.00 ± 0 | 44.60 ± 36.90 |
|  | Post 3 | 4.82 ± 2.59 | 26.3 ± 45.55 | 0 | 0 | 112.00 ± 0 | 8.50 ± 14.72 |
|  | Post 4 | 36.1 ± 17.43 | 74.57 ± 28.81 | 0 | 0 | 151.60 ± 52.64 | 2.00 ± 3.46 |
| Group 3 | Pre | 0.2 ± 0.35 | 0 | 0 | 27.07 ± 46.88 | 0.8 ± 1.39 | 65.00 ± 112.58 |
|  | Post 1 | 0.2 ± 0.35 | 0 | 0 | 0 | 0.8 ± 1.39 | 0 |
|  | Post 2 | 0 | 14.6 ± 25.29 | 6.47 ± 5.98 | 0 | 0.67 ± 0.59 | 0 |
|  | Post 3 | 19.4 ± 13.4 | 130.33 ± 89.49 | 10.63 ± 8.08 | 0 | 0.37 ± 0.65 | 0 |
|  | Post 4 | 74.2 ± 76.73 | 82.63 ± 5.16 | 29.03 ± 26.59 | 0 | 1.30 ± 2.25 | 0 |
| Group 4 | Pre | 0 | 0 | 0 | 21.77 ± 18.85 | ND |  |

TABLE 1-continued

ANTI-PRP RESPONSE
Solid Phase Radioimmunoassay for IgM and IgH

| | | PRP | | Diphtheria Toxoid | | Tetanus Toxoid | |
| --- | --- | --- | --- | --- | --- | --- | --- |
| | | IgG* | IgM | IgG | IgM | IgG | IgM |
| | Post 1 | 0 | 15.6 ± 27.02 | 2.67 ± 0.85 | 30.87 ± 27.14 | | |
| | Post 2 | 0 | 0 | 37.2 ± 10.94 | 26.2 ± 24.30 | | |
| | Post 3 | 0 | 0 | 210.00 ± 0 | 19.63 ± 17.06 | | |
| | Post 4 | 0 | 0 | 298.27 ± 207.70 | 0 | | |
| Group 5 | Pre | 0 | 0 | ND | | | |
| | Post 1 | 0 | 0 | | | | |
| | Post 2 | 0 | 0 | | | | |
| | Post 3 | 0 | 0 | | | | |
| | Post 4 | 0 | 0 | | | | |
| Group 6 | Pre | 0 | 0 | 0 | 0 | | |
| | Post 1 | 6.23 ± 2.56 | 135.00 ± 81.41 | 0 | 0 | | |
| | Post 2 | 54.2 ± 14.73 | 182.00 ± 0 | 0.93 ± 1.62 | 0 | | |
| | Post 3 | 57.6 ± 22.91 | 182.00 ± 0 | 3.05 ± 4.31 | 0 | | |
| | Post 4 | 39.6 ± 25.17 | 91.20 ± 0 | 5.95 ± 8.41 | 0 | | |

*IgG and IgM are expressed as ug antibody per ml of serum. All value are mean and standard error.
Ig levels below the sensitivity of the assay were tested as zero (0). If levels higher than the range of the assay were assigned a value equal to the upper limit of the assay.
%ND = Not Done.

What is claimed is:

1. A water-soluble covalent polysaccharide-diphtheria toxoid conjugate
   capable of producing T-cell dependent antibody responce to polysaccharide from *Haemophilus influenzae b*,
   of molecular size above 140,000 and below 4,500,000 dalton, and
   of a ribose/protein ratio between 0.25 and 0.75,
   prepared by mixing adipic hydrazide derivatized diphtheria toxoid in a substantially cyanogen halide-free solution with a cyanogen halide activated capsular *Haemophilus influenzae* b polysaccharide consisting of approximately equal parts of ribose, ribitol and phosphate, which had previously been sized by heating until more than 60% of the polysaccharide was adjusted to a molecular size between 200,000 and 2,000,000 dalton.

2. A conjugate of claim 1, wherein said halide is the bromide.

3. A process for producing a water-soluble covalent polysaccharide-diphtheria toxoid conjugate capable of producing T-cell dependent antibody responsive to polysaccharide from *Haemophilus influenzae* b
   of molecular size between 140,000 and 4,500,000 dalton, and
   of a ribose/protein ratio between 0.25 and 0.75,
   which comprises
   (a) heating a capsular polysaccharide of *Haemophilus influenzae* b consisting of approximately equal parts of ribose, ribitol and phosphate until less than 20% is of a molecular size below 200,000 dalton and less than 20% is of a size above 2,000,000 dalton;
   (b) activation of the resulting sized polysaccharide with cyanogen bromide;
   (c) removal of substantially all the unreacted cyanogen bromide; and
   (d) agitation of the activated product with adipic hydrazide derivatized diphtheria toxoid.

* * * * *